United States Patent [19]

Duquette

[11] Patent Number: 5,230,706
[45] Date of Patent: * Jul. 27, 1993

[54] BI-DIRECTIONAL VALVE ASSEMBLY USED IN NEEDLELESS INJECTION OR INFUSION PORTS

[76] Inventor: Irene A. Duquette, 172 Punkup Rd., Oxford, Conn. 06483

[*] Notice: The portion of the term of this patent subsequent to Sep. 17, 2008 has been disclaimed.

[21] Appl. No.: 850,355

[22] Filed: Mar. 12, 1992

[51] Int. Cl.⁵ ............................................. A61M 37/00
[52] U.S. Cl. ........................................ 604/83; 604/256
[58] Field of Search ............... 604/247, 246, 83, 86, 604/284, 256, 249

[56] References Cited

U.S. PATENT DOCUMENTS

| | | | |
|---|---|---|---|
| D. 296,592 | 7/1988 | Wellenstam | D24/53 |
| 2,999,499 | 9/1961 | Willet | 128/214 |
| 3,416,567 | 12/1968 | Von Dardel et al. | 137/604 |
| 3,994,293 | 11/1976 | Fero | 128/214 R |
| 4,121,585 | 10/1978 | Becker, Jr. | 128/214 R |
| 4,333,455 | 6/1982 | Bodicky | 128/214.4 |
| 4,535,820 | 8/1985 | Raines | 137/854 |
| 4,585,435 | 4/1986 | Vaillancourt | 604/27 |
| 4,596,557 | 6/1986 | Pexa | 604/284 |
| 4,661,110 | 4/1987 | Fortier et al. | 604/256 |
| 4,752,287 | 6/1988 | Kurtz et al. | 604/99 |
| 4,793,351 | 12/1988 | Landman et al. | 128/344 |
| 4,816,020 | 3/1989 | Brownell | 604/97 |
| 4,834,716 | 5/1989 | Ogle, II | 604/192 |
| 4,915,687 | 4/1990 | Sivert | 604/83 |
| 4,954,130 | 9/1990 | Edwards | 604/169 |
| 5,049,128 | 9/1991 | Duquette | 604/83 |

OTHER PUBLICATIONS

"Despite Safety Guidelines, Various Devices Still Cause Needle-Stick Injuries", *Oncology Nurse Bulletin*, vol. 10, Oct. 1988, pp. 2-8.
"Avoiding Needle-Stick Injuries", *Nursing 90*, Jan. 1990, pp. 61-64.

*Primary Examiner*—John D. Yasko
*Attorney, Agent, or Firm*—Ailes, Ohlandt & Greeley

[57] ABSTRACT

A bi-directional valve assembly disposed within an infusion system to permit the administration of an infusion solution without the use of a needle, the bi-directional valve assembly is a two-way spring valve which comprises: a spring means, a valve port, and a valve plunger having a sealing means and a conduit means disposed thereabout, wherein the spring means is connected to the valve plunger in such a way as to permit the opening of the conduit means when the spring means is recoiled such that the sealing means is not in contact with the valve port and to permit the closing of the conduit means when the spring means is expanded such that the sealing means is in contact with the valve port; whereby the bi-directional valve assembly is capable of opening and closing the infusion system.

19 Claims, 7 Drawing Sheets

BI-DIRECTIONAL VALVE ASSEMBLY USED IN NEEDLELESS INJECTION OR INFUSION PORTS

The present invention relates primarily to a bi-directional valve assembly disposed within infusion systems so that infusion solutions may be injected into intravenous tubes via a syringe or secondary tubing without the use of a needle. This bi-directional valve assembly is set forth in U.S. Pat. No. 5,049,128 (Duquette) which issued on Sep. 17, 1991, to the same inventor hereof. The valve completely eliminates the possibility of infections, e.g., hepatitis B or AIDS, resulting from needle sticks caused by use of infusion systems requiring needles for accessing intravenous tubing, valve infusion port locks (e.g., saline or heparin locks), multilumen catheter or central lines, peripheral lines, and piggyback administration systems. This unique bi-directional valve assembly can also be used in nasogastic tubing and percutaneous endogastric tuging to enable the periodic removal of bodily fluids while preventing unimpeded discharge thereof.

BACKGROUND OF THE INVENTION

The current practice necessitites the use of a needle through a self sealing rubber stopper. This is demonstrated in the Click Lock TM I.V. system manufactured by ICU Medical, Inc. which can be used with either a heparin lock or a multilumen central line. (See I.V. Therapy, *Nursing*, May 1989, pg. 50). The Click Lock TM intravenous (I.V.) system has two components: a transparent housing that contains a recessed needle and a diaphragm-covered port that fits into the needle housing. A locking device on the needle housing then clicks over a flange at the base of the port, securing the components as the needle pierces the diaphragm. The Click Lock TM I.V. system can be used to piggyback an I.V. into regular I.V. tubing, a heparin lock, or a central line.

Figure 7:
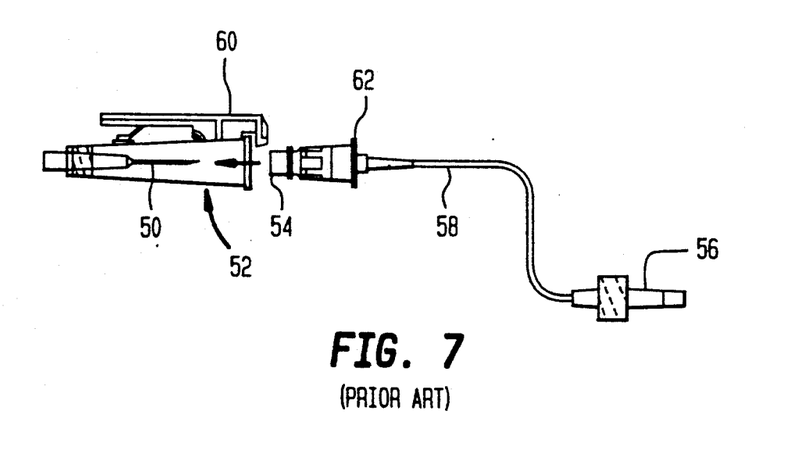
FIG. 7 is a schematic representation of a conventional valve infusion port device having a stopper at one end for connecting with a needle disposed within a Click-Lock ™ device.

Use of the Click Lock TM I.V. system with a heparin lock is shown in FIG. 7, attached hereto, wherein a needle 50 contained within housing 52 is typically injected into a rubber diaphragm injection port 54. A locking device 60 disposed on housing 52 clicks over a flange 62 at the base of injection port 54. Thereafter, injection port 54 is connect to a luer lock device 56 by means of I.V. tubing 58. Luer lock device 56 can thereafter be connected to a catheter, not shown.

Some other examples demonstrating the use of needles at I.V. injection units are U.S. Pat. Nos. 4,121,585 (Becker, Jr.), issued Oct. 24, 1978, 4,585,435 (Vaillancourt), issued Apr. 29, 1986, and 4,596,557 (Pexa), issued Jun. 24, 1986.

The health risk associated with needle sticks has become of great concern to the medical community. This is evidenced by the recently published article, "Despite Safety Guidelines, Various Devices Still Cause Needle-Stick Injuries," *Oncology Nurse Bulletin*, (NCM Publishers, Inc.), Oct. 1988, pp. 2 and 8. This article discusses the complacency about needle sticks which causes approximately 300 healthcare workers to die each year from direct or indirect consequences of occupational acquired hepatitis B, not to mention the number which test positive each year to AIDS testing. The article continues to state that "the second most common cause of needle sticks, and the biggest rate of injury, came from accidents involving intravenous tubing needle assemblies". In these accidents, over one quarter were related to recapping, and this was probably due to the fact that the needle caps were unavailable when intravenous lines were dismantled. The needle sticks occurred when alternative methods, such as introducing needles into drip chambers, intravenous ports or bags, were used for covering the needles.

Thus, needle sticks can occur from recapping of needles, poor needle connections, attempts at removal of a needle by loosening of the needle hub from the tubing, and when the needle is either manually or accidental dislodged from the tubing.

Any injury from a used needle is potential for infection, especially hepatitis B and AIDS. Conventional infusion ports typically include a polyvinylchloride primary infusion tubing, an infusion port, and self sealing rubber stopper. During administration of a medication or other solutions a needle is injected into self sealing rubber stopper located about the opening of the infusion port.

Needle sticks occur during the injection and withdrawal of the needle from the stopper, and at most anytime when the needle is uncapped, transported or disposed. Since intravenous injections are common place in medical treatment, it is entirely to risky to continue to expose medical personnel to needle sticks which can lead to the contraction of infectious diseases.

The present inventor has developed a unique bi-directional valve assembly which does not require the use of needles to deliver a transfusional or perfusional liquid, a nourishing solution, a vitamin solution, a medicinal solution, an anticoagulant solution or a like solution, to infusion systems (e.g., I.V. systems), thereby completely eliminating the threat of contracting infectious diseases when the solution is administered via the system. It also prevents escape of contaminated blood or other bodily fluids through, for example, an I.V. tubing, thus further reducing the risk to healthcare professionals.

One device which attempts to eliminate the use of needles during the administration of secondary medications or blood transfusions to a Y-shaped injection unit of an I.V. system is set forth in U.S. Pat. No. 3,994,293 (Ferro), issued Nov. 30, 1976. The Ferro patent describes an injection assembly which can be used in combination with a feeding means (e.g., a syringe) for infusing a transfusional or perfusional liquid, a nourishing solution, a vitamin solution, a medicinal solution, an anticoagulant solution or a like solution, wherein penetration of a hollow piercing member (e.g., a syringe needle) into the injector body is not necessary. The purpose of the device set forth in the Ferro patent is to overcome the disadvantages caused by repeatedly injecting new needles into the injector wall. That is, after repeated injections the injector wall weakens and is no longer adequately sealed.

The Ferro patent makes use of a liquid pressure-actuated elastomeric diaphragm positioned in the tubular branch portion. The diaphragm includes a pre-perforated portion formed having a pressure threshold corresponding to a predetermined pressure of the solution upstream of the diaphragm. The pre-perforated portion is normally impervious to prevent passage of the solution through the tubular branch portion of the tubular conduit portion when the pressure of the solution upstream of the diaphragm is less than the pressure threshold. The pre-perforated portion becomes pervious to allow passage of the solution through the tubular branch portion to the tubular conduit portion when the pressure of the solution upstream of the diaphragm is at least equal to or greater than the pressure threshold. Furthermore, a valve means cooperating with the pre-perforated portion of the diaphragm only permits unidirectional feeding of the solution in the tubular portion through the pre-perforated portion to the tubular conduit portion, but not vice versa.

One disadvantage of the injector assembly set forth in the Ferro patent is that it causes air in the tubing and does not permit bi-directional movement of the pre-perforated portion of the diaphragm.

The Safsite ™ reflux valve manufactured by B. Braun is similar to the Ferro patent in that it replaces injection stoppers with a needless reflux valve. This reflux valve includes a flexible diaphragm which is opened by standard luer taper permitting injection, gravity flow or withdrawal of fluids. Reflux valves can be used for piggy-back administration or for accessing a multi-lumen catheter or central line, peripheral line or heparin lock. (See U.S. Pat. No. 4,535,820 (Raines), which issued on Aug. 20, 1985).

Various needleless syringe assemblies have been designed for use in catheter devices, e.g., U.S. Pat. Nos. 4,752,287 (Kurtz et al.), issued Jun. 21, 1988, 4,816,020 (Brownell), issued Mar. 28, 1989, and 4,333,455 (Bodicky), issued Jun. 8, 1982. These devices are concerned with inflation of catheter ballons and not the injection of medicines or other solutions into an intravenous system.

The present invention overcomes the aforementioned disadvantages of conventional infusion systems by providing a device which eliminates the use of needles and injection port stoppers in the administration of a transfusional or perfusional liquid, a nourishing solution, a vitamin solution, a medicinal solution, an anticoagulant solution or a like solution, via an injection port. The present invention also completely eliminates the risk of contracting an infectious disease due to needle sticks during the handling of infusion systems.

The present invention accomplishes the aforementioned advantages by positioning a novel two-way spring valve within intravenous tubing, valve infusion port locks (e.g., saline or heparin locks), multilumen catheter or central lines, peripheral lines, and piggyback administration systems to permit administration of a transfusional or perfusional liquid, a nourishing solution, a vitamin solution, a medicinal solution, an anticoagulant solution or a like solution without the injection of a needle and permits bi-directional movement of the valve to avoid backflow of solution or air contamination of the infusion system. This unique bi-directional valve assembly can also be used in nasogastric tubing and percutaneous endogastric tubing to enable the periodic removal of bodily fluids while preventing unimpeded discharge thereof.

Additional advantages of the present invention shall become apparent as described below.

SUMMARY OF THE INVENTION

A bi-directional valve assembly disposed within an infusion system to permit the administration of an infusion solution without the use of a needle. The bi-directional valve assembly is a two-way spring valve which comprises: a spring means, a valve port, and a valve plunger having a sealing means and a conduit means disposed thereabout, wherein the spring means is connected to the valve plunger in such a way as to permit the opening of the conduit means when the spring means is recoiled such that the sealing means is not in contact with the valve port and to permit the closing of the conduit means when the spring means is expanded such that the sealing means is in contact with the valve port; whereby the bi-directional valve assembly is capable of opening and closing the infusion system.

The bi-directional valve assembly is a two-way spring valve which allows an infusion solution to flow freely through the valve into the infusion system and upon removal of the syringe or tubing the valve closes to keep air out of the infusion system and prevent the infusion solution from leaking out through the valve. This valve is also capable of permitting the removal of infusion or bodily fluids through the infusion port without detriment to the infusion system.

This valve can be used in nasogastric tubing and percutaneous endogastric tubing to enable the periodic removal of bodily fluids while preventing unimpeded discharge thereof.

An additional object of the present invention is the application of a closing means about the bi-directional for keeping it sterile. The closing means is typically a cap or stopper.

The present invention may also include many additional features which shall be further described below.

BRIEF DESCRIPTION OF THE DRAWINGS

FIG. 3a is a side view of the valve plunger with integral sealing means as depicted in FIG. 2a.

DESCRIPTION OF THE PREFERRED EMBODIMENTS

An infusion system which includes a two-way spring valve assembly capable of permitting access to the primary infusion by a syringe or secondary tubing without the use of a needle. This valve infusion port completely eliminates the possibility of infections, e.g., hepatitis B or AIDS, resulting from needle sticks caused by use of infusion systems requiring needles for accessing the primary infusion with a secondary medication or other solution.

This bi-directional valve assembly is also capable of being disposed within nasogastric tubing and percutaneous endogastric tubing to enable the periodic removal of bodily fluids while preventing unimpeded discharge thereof.

The present invention provides for the needleless injection of a secondary infusion into a Y-shaped injection unit by attaching a syringe, leur lock tubing or straight intravenous secondary tubing to a bi-directional valve of a secondary infusion port. The valve secondary infusion port also maintains a closed system in the intravenous line, i.e., keeps fluid in and air out.

Figure 1:
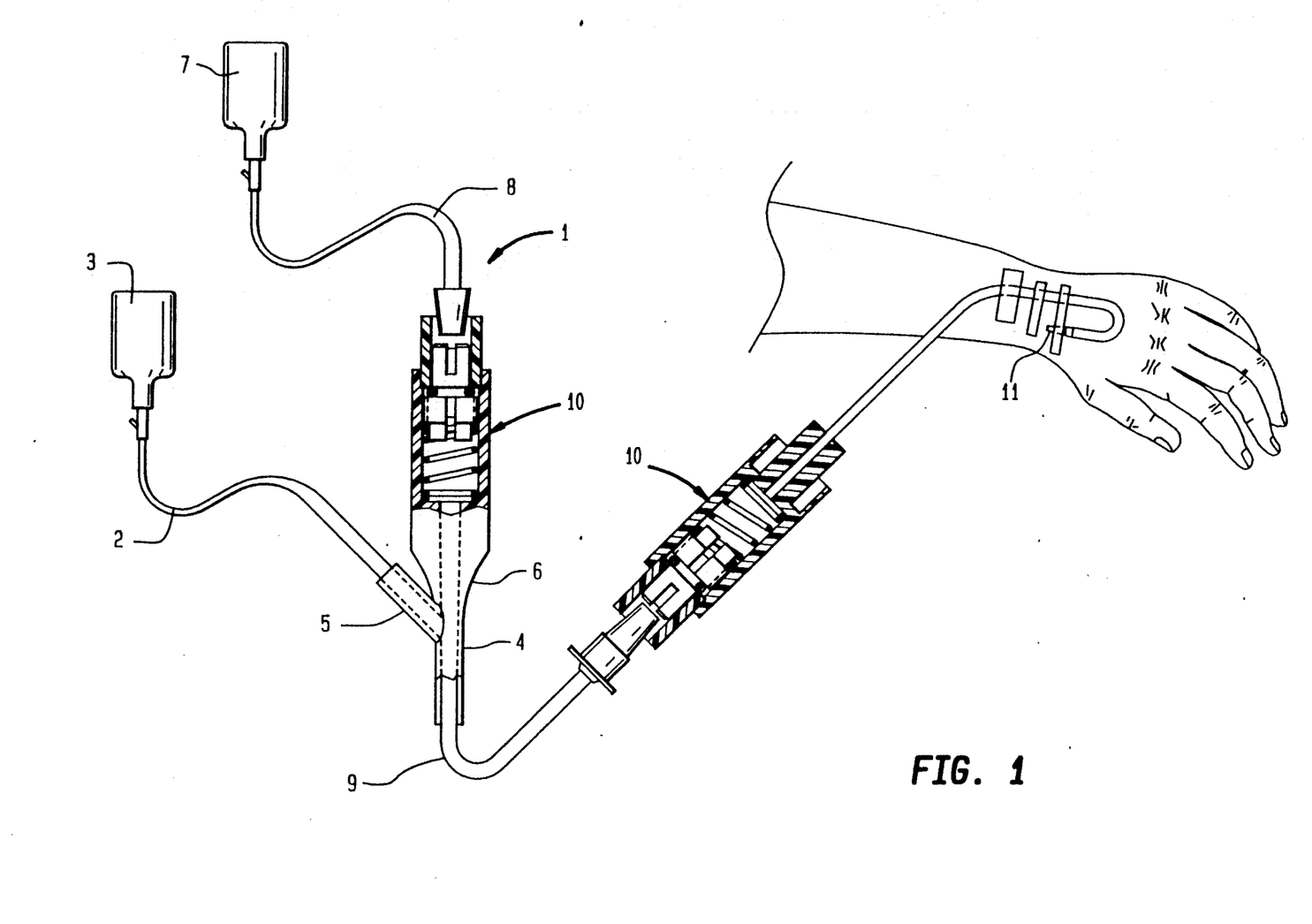
FIG. 1 is a schematic representation of an infusion system according to the present invention wherein a bi-directional valve assembly is disposed between a needle and a Y-shaped injection unit, and, optionally, between the Y-shaped injection unit and a means for secondary medication administration.

The present invention can best be described by referring to the attached drawings. FIG. 1 depicts an intravenous or infusion system 1 which comprises primary tubing 2, primary solution bottle 3 and Y-shaped injection unit 4. Y-shaped injection unit 4 includes primary infusion port 5 and secondary infusion port 6. Primary tubing 2 is connected to Y-shaped injection unit 4 via primary infusion port 5. Primary tubing 2 is affixed to Y-shaped injection unit 4 at primary infusion port 5 by any suitable means, including, but not limited to, heat sealing.

Secondary infusion port 6 which includes a bi-directional or two-way valve assembly 10 is used to introduce a secondary medication or solution contained in secondary solution bottle 7 into Y-shaped injection unit 4. Use of two-way valve 10 allows the administration of secondary medication or solution from secondary solution bottle 7 without the use of a needle. That is, two-way valve 10 opens to allow the secondary infusion to flow freely through secondary infusion port 6 into Y-shaped injection unit 4, and closes when the secondary infusion means is removed thereby keeping air out and preventing primary infusion administered from primary solution bottle 3 from leaking out through secondary infusion port 6.

By using the valve infusion port of the present invention the danger of needle stick injury to medical personnel during administration and removal of the secondary infusion to an intravenous system is eliminated.

During normal administration of a secondary infusion, primary bottle 3 is lowered to below the base of secondary bottle 7. Secondary bottle 7 empties via gravity flow through secondary tubing 8, Y-shaped injection unit 4, intravenous tubing 9, and needle 11 into the patient. When secondary bottle 7 is empty administration of the primary infusion via primary bottle 3 is resumed without interruption.

FIG. 1 also includes a second bi-directional or two-way valve assembly 10 disposed within intravenous tubing 9 between needles 11 and Y-shaped injection unit 4. Use of two-way valve 10, as shown in FIG. 1, permits the needleless replacement or substitution of piggy-back administration devices.

Figure 2:
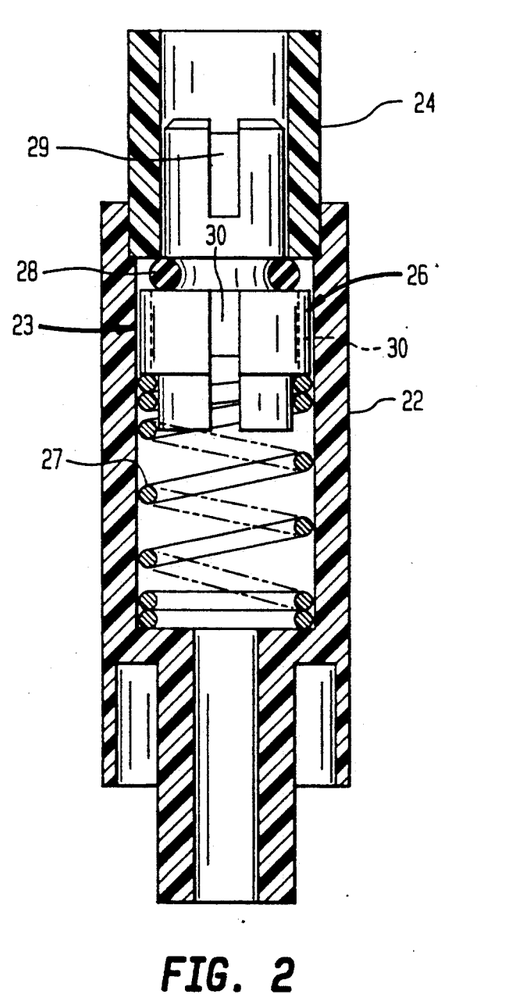
FIG. 2 is a schematic representation of the bi-directional valve assembly according to the present invention.

FIG. 2 shows bi-directional valve assembly 23 disposed directly within valve infusion port 22. Optionally, bi-directional valve assembly 23 can be disposed within a valve housing (not shown) which is then connected to an infusion port. As such, it is to be clearly understood that any suitable bi-directional valve assembly may be used and that the valve may be disposed either within valve infusion port 22 or simply attached thereto within a valve housing (not shown). A unique feature of bi-directional valve assembly 23 is that it permits access to the primary infusion by a secondary infusion via a syringe or secondary tubing without the use of a needle.

It is preferable that bi-directional valve assembly 23 be a two-way spring valve which opens to allow an infusion to flow freely through valve infusion port 22 into an infusion system and closes upon removal of a syringe or intravenous tubing to keep air out of the infusion system and also to prevent the infusion from leaking out through valve infusion port 22.

A closing means, not shown, is preferably disposed about valve infusion port 22 and bi-directional valve assembly 23 for keeping air out of the infusion system and maintaining sterility. The closing means can be any suitable device, e.g., a plastic flip-top cap or stopper.

FIG. 2 also depicts a preferred two-way spring valve 23 which includes a valve plunger 26, a spring means 27, a valve port 24, sealing means 28, and conduit means (29, 30) which are capable of transporting infusion solution into the infusion system.

Spring means 27 is connected to valve plunger 26 in such a way as to permit the opening and closing of conduit means (29, 30). That is, as valve plunger 26 is depressed toward infusion port 22 by an infusion means (not shown) spring means 27 recoils such that sealing means 28 is no longer in contact with valve port 24, thereby opening conduit means (29, 30) and allowing an infusion solution to flow from valve port 24 through conduit means (29, 30) into the infusion system.

Conversely, as the infusion means is removed from valve port 24 spring means 27 expands such that valve plunger 26 moves away from infusion port 22 such that sealing means 28 comes in contact with valve port 24, thereby closing conduit means (29, 30), and preventing air contamination or backflow or infusion solution or bodily fluids through infusion port 22.

Figure 2A:
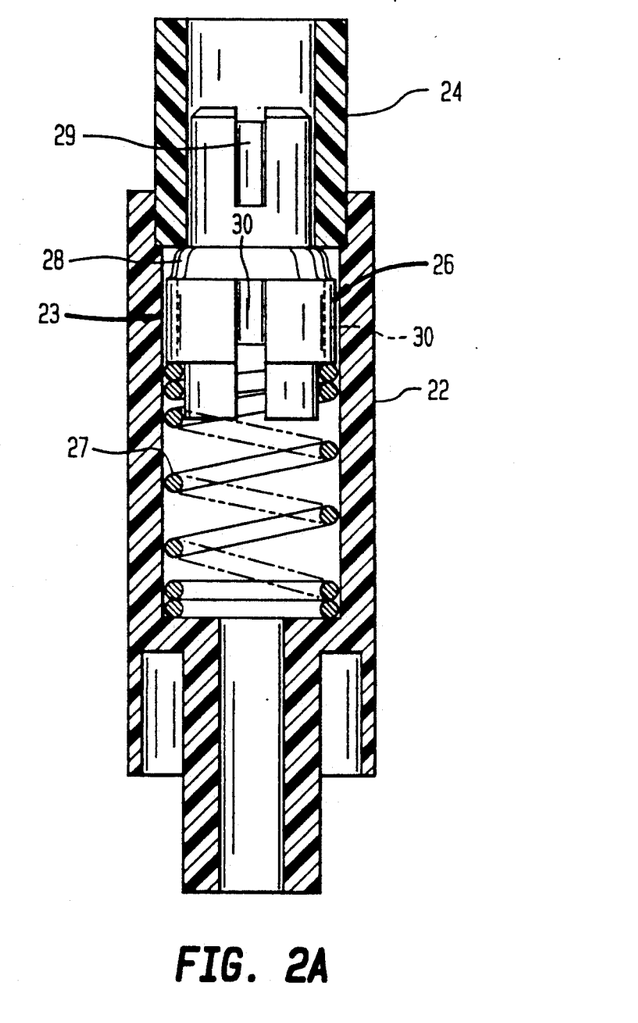
FIG. 2a is a schematic representation of the bi-directional valve assembly wherein the sealing means is formed as an integral part of the valve plunger.

Spring means 27 is preferably made from surgical grade stainless steel. Sealing means 28 is typically a rubber or plastic O-ring seal which is either a separate piece or integrally molded together with valve plunger 26 (See FIGS. 2a and 3a). And the remaining components of valve 23 are preferably made of non-allergic plastics or other suitable materials. In the instance where a valve housing is used it would also be formed from non-allergic plastics.

Figure 3:
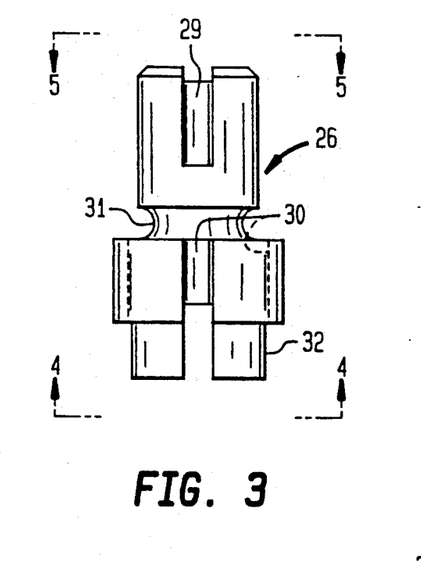
FIG. 3 is a side view of the valve plunger depicted in FIG. 2.
Figure 3A:
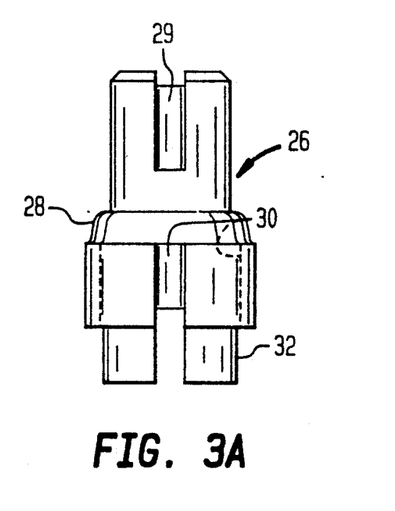
Figure 4:
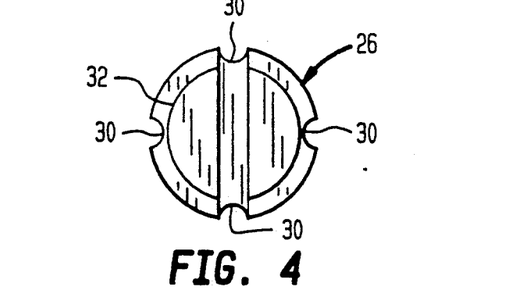
FIG. 4 is a bottom planar view along line 5—5 of FIG. 3.
Figure 5:
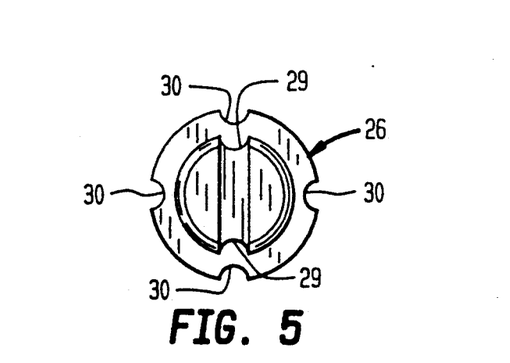
FIG. 5 is a top planar view along line 6—6 of FIG. 3.

FIG. 3 depicts valve plunger 26 having conduit means (29, 30) molded therein. The sealing means, not shown, is disposed about concave portion 31 and spring means, not shown, is attached to valve plunger 26 about portion 32 thereof. FIG. 4 is a button planar view along line 5—5 of FIG. 3 and shows valve plunger 26 with conduit means 30. FIG. 5 is a top planar view along line 6—6 of FIG. 3 and shows valve plunger 26 and conduit means (29, 30).

Figure 6:
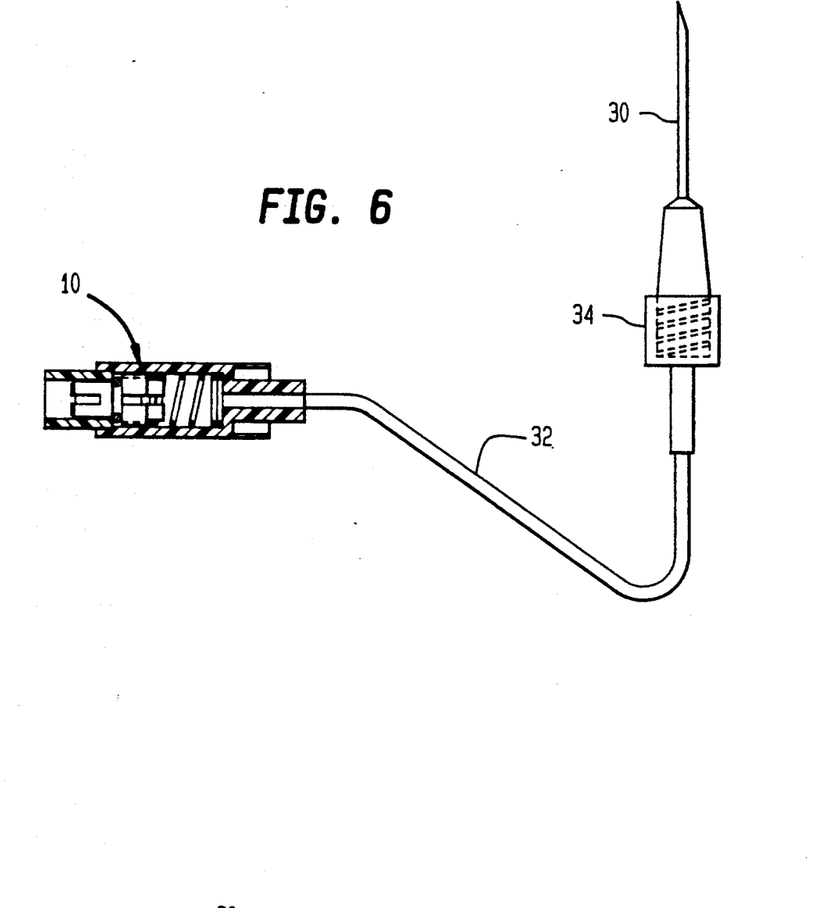
FIG. 6 is a schematic representation of the bi-directional valve assembly disposed within a valve infusion port lock device.

FIG. 6 demonstrates the use of a bi-directional valve assembly 10 at one end of a valve infusion port lock, i.e., a saline lock or heparin lock. Bi-directional valve assembly 10 is connected to a needle 30 or catheter (not shown) by intravenous tubing 32. Preferably, needle 30 is mounted within a leur lock device 34. Although not show in this drawing, bi-directional valve assembly 10 may include a leur lock device about its end opposite intravenous tubing 32.

Figure 8:
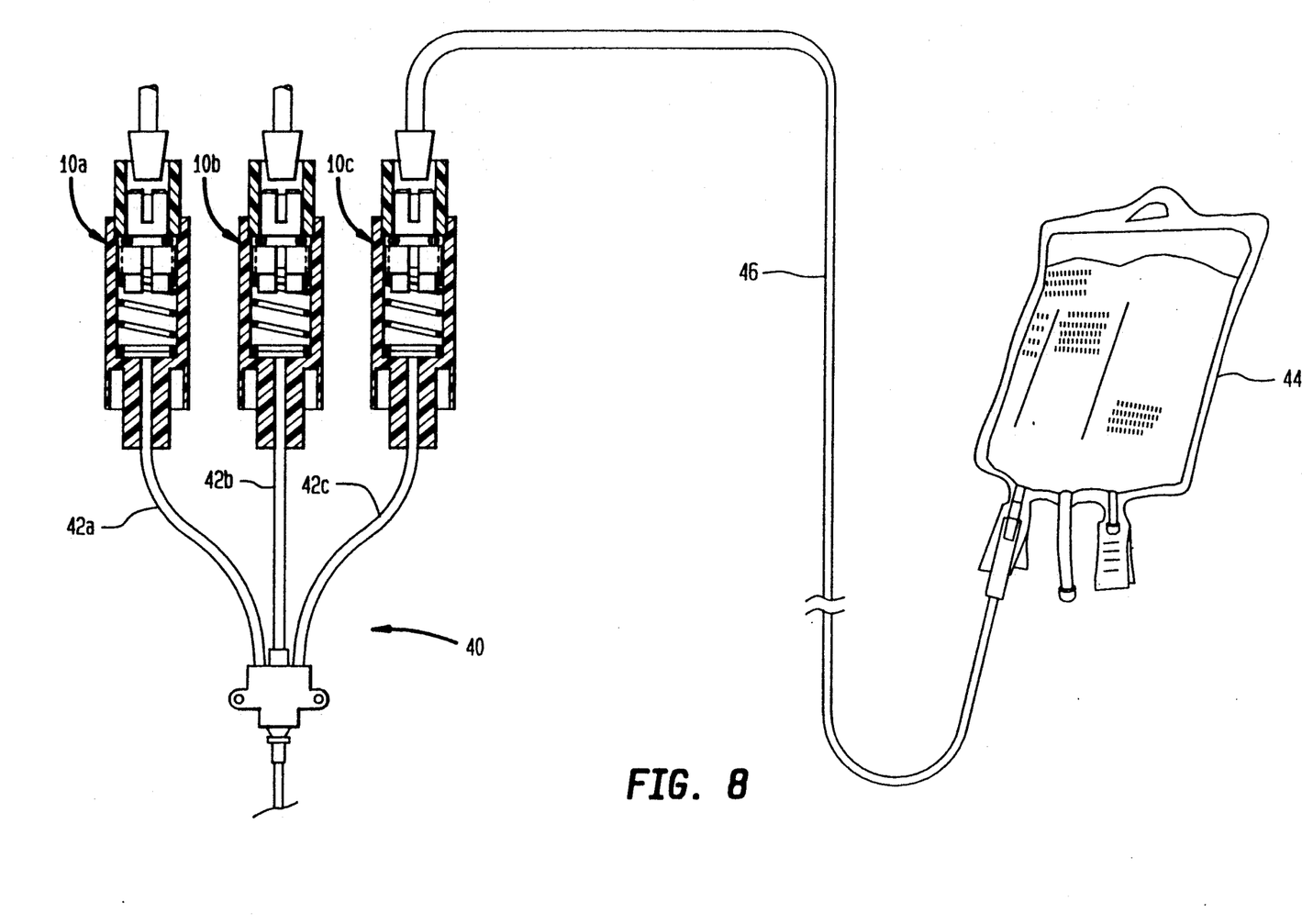
FIG. 8 is a schematic representation of a multilumen catheter or central lines device having a bi-directional valve assembly disposed within each line.

FIG. 8 depicts the use of multiple bi-directional valve assemblies 10a, 10b, and 10c within an infusion system 40 which comprises multilumen catheter or central lines 42a, 42b and 42c. The bi-directional valves can thereafter by connected to various infusion bottles, syringes or the like in order to supply infusion system 40 with the desired infusion solutions. For example, an infusion bottle 44 is connected to bi-directional valve assembly 10c by means of intravenous tubing 46.

Figure 9:
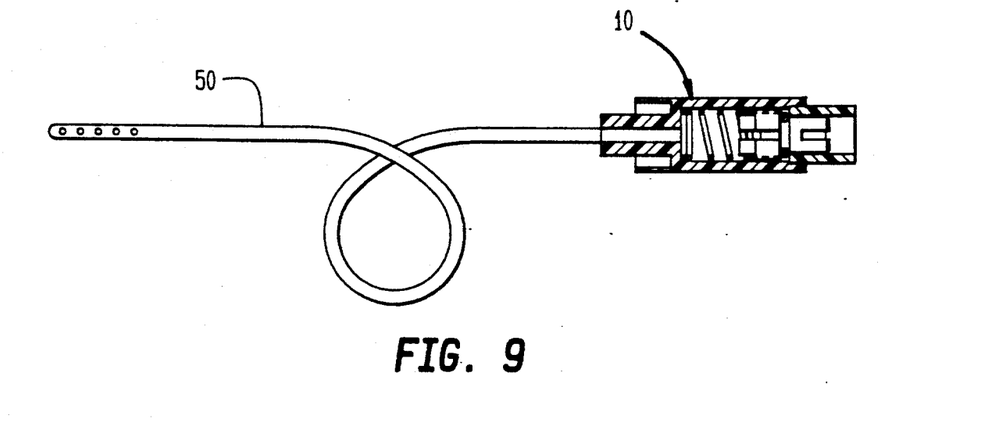
FIG. 9 is a schematic representation of a bi-directional valve assembly disposed within a nasogastric tubing.
Figure 10:
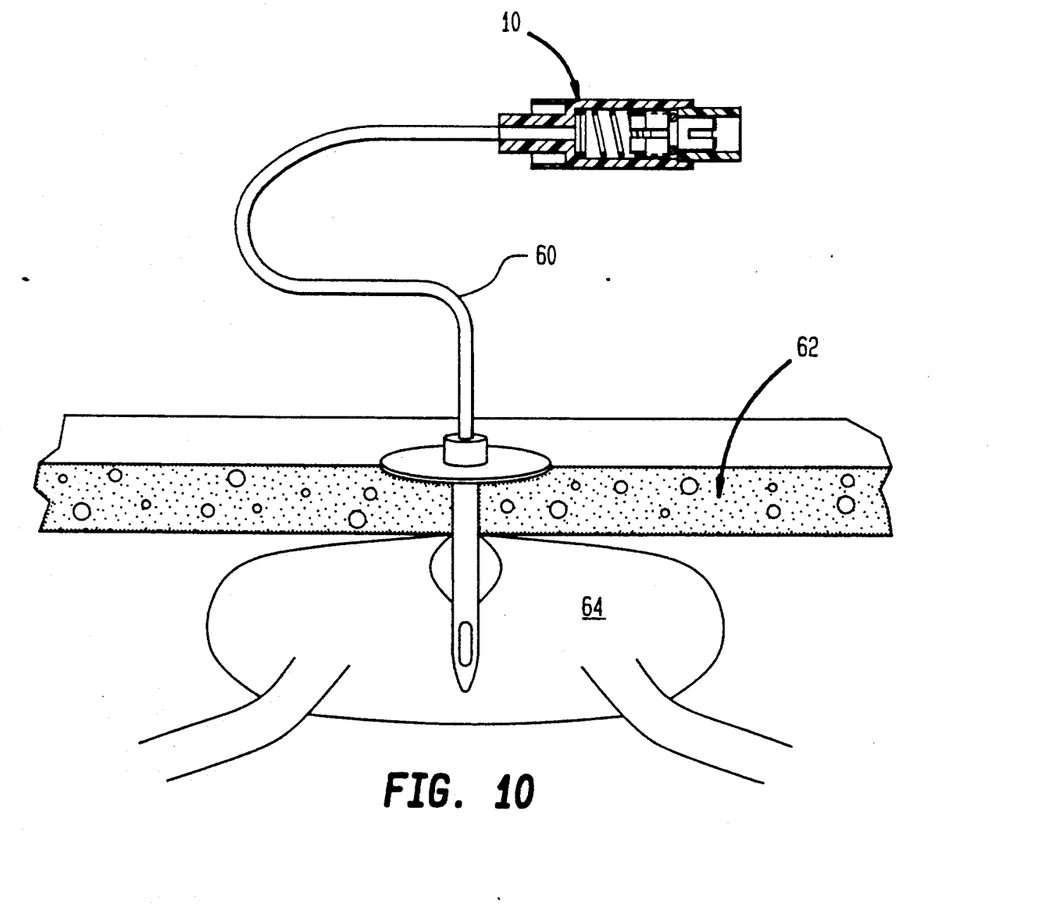
FIG. 10 is a schematic representation of a bi-directional valve assembly disposed within a percutaneous endogastric tubing.

FIG. 9 demonstrates the use of a bi-directional valve assembly 10 with nasogastric tubing 50. FIG. 10 shows the application of a bi-directional valve assembly 10 with percutaneous endogastric tubing 60. Endogastric tubing 60 passes through the tissue layer 62 of the patient and into stomach 64. Bi-directional valve assembly 10 is capable of permitting periodic removal of bodily fluids from either tubing while preventing unimpeded discharge thereof.

While I have shown and described several embodiments in accordance with my invention, it is to clearly understood that the same are susceptible to numerous changes and modifications apparent to one skilled in the art. Therefore, I do not wish to be limited to the details shown and described but intend to show all changes and modifications which come within the scope of the appended claims.

What is claimed is:

1. A bi-directional valve assembly disposed within an infusion system to permit the administration of an infusion solution without the use of a needle, said bi-directional valve assembly is a two-way spring valve which comprises: a spring means, a valve port, and a valve plunger having a sealing means and a conduit means disposed thereabout, wherein said spring means is connected to said valve plunger in such a way as to permit the opening of said conduit means when said spring means is recoiled such that said sealing means is not in contact with said valve port and to permit the closing of said conduit means when said spring means is expanded such that said sealing means is in contact with said valve port; whereby said bi-directional valve assembly is capable of opening and closing said infusion system.

2. The bi-directional valve assembly according to claim 1 wherein said infusion solution is either a transfusional or perfusional liquid, a nourishing solution, a vitamin solution, a medicinal solution, or an anticoagulant solution.

3. The bi-directional valve assembly according to claim 1 wherein said infusion system comprises at least one element selected from the group consisting of: intravenous tubing, valve infusion port locks, multilumen catheter or central lines, peripheral lines, and piggyback administration systems.

4. The bi-directional valve assembly according to claim 3 wherein said valve infusion port locks are either saline locks or heparin locks.

5. The bi-directional valve assembly according to claim 1 wherein said bi-directional valve is connected to either a syringe, a leur lock tubing, or an intravenous tubing.

6. The bi-directional valve assembly according to claim 1 wherein said spring means is a stainless steel spring.

7. The bi-directional valve assembly according to claim 1 wherein said valve plunger and valve port are formed from plastic, non-allergic plastic or rubber.

8. The bi-directional valve assembly according to claim 1 wherein said sealing means is a rubber or plastic O-ring seal.

9. The bi-directional valve assembly according to claim 1 wherein said conduit means are formed on said valve plunger.

10. The bi-directional valve assembly according to claim 1 wherein said sealing means is formed as an integral part of said valve plunger.

11. The bi-directional valve assembly according to claim 1 further comprising a valve housing.

12. A bi-directional valve assembly disposed within nasogastric tubing or percutaneous endogastric tubing to enable the periodic removal of bodily fluids while preventing unimpeded discharge of said fluids, said bi-directional valve assembly is a two-way spring valve which comprises: a spring means, a valve port, and a valve plunger having a sealing means and a conduit means disposed thereabout, wherein said spring means is connected to said valve plunger in such a way as to permit the opening of said conduit means when said spring means is recoiled such that said sealing means is not in contact with said valve port and to permit the closing of said conduit means when said spring means is expanded such that said sealing means is in contact with said valve port; whereby said bi-directional valve assembly is capable of opening and closing said nasogastric tubing or said percutaneous endogastric tubing.

13. The bi-directional valve assembly according to claim 12 wherein said bi-directional valve is connected to either a syringe, a leur lock tubing, or an intravenous tubing.

14. The bi-directional valve assembly according to claim 12 wherein said spring means is a stainless steel spring.

15. The bi-directional valve assembly according to claim 12 wherein said valve plunger and valve port are formed from plastic, non-allergic plastic or rubber.

16. The bi-directional valve assembly according to claim 12 wherein said sealing means is a rubber or plastic O-ring seal.

17. The bi-directional valve assembly according to claim 12 wherein said conduit means are formed on said valve plunger.

18. The bi-directional valve assembly according to claim 12 wherein said sealing means is formed as an integral part of said valve plunger.

19. The bi-directional valve assembly according to claim 12 further comprising a valve housing.

* * * * *